United States Patent
Donohue et al.

(10) Patent No.: US 8,003,390 B2
(45) Date of Patent: Aug. 23, 2011

(54) RESPONSES TO SINGLET OXYGEN

(75) Inventors: Timothy J. Donohue, Milddleton, WI (US); Jennifer Rachel Anthony, San Lorenzo, CA (US); Kristin L. Warczak, Franklin, WI (US); Yann Dufour, Madison, WI (US); Heather Green, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 428 days.

(21) Appl. No.: 11/410,431

(22) Filed: Apr. 25, 2006

(65) Prior Publication Data

US 2007/0004043 A1 Jan. 4, 2007

Related U.S. Application Data

(60) Provisional application No. 60/674,470, filed on Apr. 25, 2005.

(51) Int. Cl.
*C12N 15/74* (2006.01)
*C12N 1/20* (2006.01)
(52) U.S. Cl. ..................... 435/471; 435/252.1
(58) Field of Classification Search ................ None
See application file for complete search history.

(56) References Cited

OTHER PUBLICATIONS

Newman et al., J. Mol. Biol. 1999, 294, 307-320.*
Anthony et al., J. Mol. Biol., 2004, 341, 345-360.*
Richards, Cell. Mol. Life Sci., 1997, 53:790-802.*

* cited by examiner

*Primary Examiner* — Nancy Vogel
(74) *Attorney, Agent, or Firm* — Quarles & Brady LLP

(57) ABSTRACT

The physiological response of a phototroph to singlet oxygen is altered by modulating the interaction between an anti-sigma factor, ChrR, and a sigma factor, $\sigma^E$, or by altering expression of a gene product required for viability in the presence of singlet oxygen.

7 Claims, 5 Drawing Sheets

RESPONSES TO SINGLET OXYGEN

CROSS-REFERENCE TO RELATED APPLICATIONS

This application claims the benefit of U.S. Provisional Patent Application No. 60/674,470, filed Apr. 25, 2005, incorporated herein by reference as if set forth in its entirety.

STATEMENT REGARDING FEDERALLY SPONSORED RESEARCH OR DEVELOPMENT

This invention was made with United States government support awarded by the following agencies No new matter has been added.: National Institute of General Medical Science, GM37509. The United States has certain rights in this invention.

BACKGROUND

The invention relates generally to modulating physiological responses to singlet oxygen in a bacterial cells, algae or plant phototrophs. Several sources of singlet oxygen in biological systems, including enzymes such as peroxidases and oxidases, as well as processes such as photosynthesis. Kochevar I, "Singlet oxygen signaling: from intimate to global," STKE 204:pe7 (2004). In the photosynthetic process, input light energy converts water ($H_2O$) and carbon dioxide ($CO_2$) to oxygen ($O_2$) and sugar. Cellular respiration subsequently converts some of the sugar into chemical energy in the form of ATP. The conversion is associated with chlorophyll, a green pigment common to all photosynthetic cells. Although $O_2$ is a relatively non-reactive chemical, when exposed to high-energy or electron-transferring chemical reactions, it can be converted to highly reactive chemical forms collectively designated as "reactive oxygen species" (ROS). ROS are generally considered toxic to organisms because they oxidize carbohydrates, DNA, lipids and proteins, breaking down normal cellular, membrane and reproductive functions. Ultimately, at toxic ROS levels, a chain reaction of cellular oxidation can result in disease or lethality.

Singlet oxygen ($^1O_2$) is an ROS produced as a photosynthetic byproduct. In phototrophs, including plants, light energy excites chlorophyll pigments in the light harvesting complexes to a triplet state. At some frequency, an energy transfer from the excited triple state chlorophyll pigments to ground-state $O_2$ generates $^1O_2$ which, as a strong oxidant, can destroy membrane integrity, abolish biomolecular function, and reduce photochemical activity by inactivating photosynthetic enzymes.

Because excited triplet-state chlorophyll pigments and ground-state oxygen are found in close proximity to one another, many phototrophs exhibit some natural defenses against $^1O_2$. For example, carotenoids, fat-soluble, anti-oxidant pigments found within the photosynthetic apparatus, quench $^1O_2$. Telfer A, "What is β-carotene doing in the photosystem II reaction centre," Phil. Tans. R. Soc. Lond. 357: 1431-1440 (2002). Carotenoids include, but are not limited to, β-carotene, zeaxanthin and tocopherols. If not completely quenched by carotenoids, $^1O_2$ can specifically trigger upregulation of genes that encode proteins involved in the molecular defense against photo-oxidative stress. For example, a network of upregulated plant genes maintains a balance between ROS-scavenging proteins and ROS-producing proteins. Mittler R, "Reactive oxygen gene network of plants," TRENDS in Plant Sci. 9:490-498 (2004). In bacteria, a set of sigma factors, interchangeable RNA polymerase subunits responsible for recognizing transcriptional promoters, maintain essential housekeeping functions and facilitate host response to specific environmental stresses, including ROS. A constitutively-expressed, principal sigma factor is responsible for transcribing essential housekeeping genes. Other sigma factors, transcriptionally- or post-translationally-activated in response to stresses, recognize promoters upstream of genes involved in the response to stresses. Sigma factors are themselves regulated by anti-sigma factors that bind to a specific sigma factor and inhibit that sigma factor's ability to recognize a promoter.

Activation of sigma factors has been studied, inter alia, in *Rhodobacter sphaeroides*, a member of the α-subdivision of Proteobacteria and a facultative phototroph. *R. sphaeroides* is among the most metabolically diverse organisms known, being capable of growth under a wide variety of growth conditions. In addition to being photosynthetic, *R. sphaeroides* possesses additional energy-acquiring mechanisms including lithotrophy, aerobic respiration and anaerobic respiration. SigmaE ($\sigma^E$), a 19.2 kDa alternative sigma factor encoded by rpoE and related to members of the extra-cytoplasmic function (ECF) subfamily of eubacterial RNA polymerase sigma factors, is increased following environmental stress in *R. sphaeroides*. $\sigma^E$ directs transcription from rpoE P1, a promoter for the rpoEchrR operon, and from cycA P3, a promoter for cytochrome $c_2$. Newman J. et al, "The *Rhodobacter sphaeroides* ECF sigma factor, $\sigma^E$, and the target promoters cycA P3 and rpoE P1," J. Mol. Biol. 294:307-320 (1999), incorporated herein by reference as if set forth in its entirety. Basal $\sigma^E$ activity, however, is quite low because it is complexed with a zinc-dependent anti-sigma factor, ChrR. ChrR loses its ability to inhibit $\sigma^E$ if zinc is removed, or if a zinc-binding domain of the N-terminal domain is removed. Newman J, et al., "The importance of zinc-binding to the function of *Rhodobacter sphaeroides* ChrR as an anti-sigma factor," J. Mol. Biol. 313:485-499 (2001), incorporated herein by reference as if set forth in its entirety.

GenBank Accession No. AAB17905 (SEQ ID NO:1), discloses the fuill-length *R. sphaeroides* ChrR sequence. ChrR with a C38R mutation prevented binding to $\sigma^E$. See Newman et al. (1999), supra. Likewise, ChrR with a C35S or a C38S mutation prevented binding to $\sigma^E$. See Newman et al. (2001), supra. Furthermore, a ChrR with a C187/189S mutation was shown to prevent binding to $\sigma^E$. Id. In addition, ChrR with a H6A mutation, a H31A mutation, a C35A mutation or a C38A mutation cannot bind zinc and ultimately cannot bind $\sigma^E$.

GenBank Accession No. AAB17906 (SEQ ID NO:2) discloses the full-length *R. sphaeroides* $\sigma^E$ sequence. Mutations in region 2.1 (amino acids 22 to 46 of SEQ ID NO:2) of $\sigma^E$ alter the interaction between ChrR and $\sigma^E$. Anthony J, et al., "Interactions between the *Rhodobacter sphaeroides* ECF sigma factor, $\sigma^E$, and its anti-sigma factor, ChrR," J. Mol. Biol. 341:345-360 (2004), incorporated herein by reference as if set forth in its entirety. In particular, $\sigma^E$ with a K38E mutation, a K38R mutation or a M42A mutation were less sensitive to ChrR both in vivo and in vitro.

Because $^1O_2$ affects many organisms (including, but not limited to, bacteria, plants, animals and humans), the components of the biological response to $^1O_2$ find application in medicine, agriculture, biotechnology and bioenergy production systems. Animals and plants use $^1O_2$ to defend against microbial pathogens. Davies M, "Reactive species formed on proteins exposed to singlet oxygen," Photochem. Photobiol. Sci. 3:17-25 (2004), incorporated herein by reference as if set forth in its entirety. For the foregoing reasons, there is a desire to manipulate physiological responses to $^1O_2$ in animals, bacteria and plants. There are many advantages of studying responses to $^1O_2$ in *R. sphaeroides*. First, one can control the formation of significant amounts of $^1O_2$. Also, biochemical and genetic systems are available to study the response to $^1O_2$ in vivo and in vitro, including an Affymetrix gene chip (Affymetrix; Santa Clara, Calif.), LC/MS proteomics and computation approaches.

BRIEF SUMMARY

The present invention relates to observations by the inventors relating to genes required for viability of *R. sphaeroides* in the presence of $^1O_2$ which can be generated during photosynthesis. Specifically, changes in the interaction between alternative sigma factor $\sigma^E$ and its anti-sigma factor ChrR affects expression of genes required for viability of *R. sphaeroides* in the presence of $^1O_2$. Although homologs of $\sigma^E$ and ChrR have been identified computationally in other bacteria, their involvement in a cellular response to $^1O_2$ has not heretofore been noted.

As the inventors detail below, $^1O_2$ typically has detrimental effects upon cells, but cells can avoid or overcome the effects by increasing $\sigma^E$, which is ordinarily complexed with ChrR. In the presence of $^1O_2$, ChrR and $\sigma^E$ dissociate and synthesis of $\sigma^E$ increases, allowing free $\sigma^E$ to bind to a core RNA polymerase, facilitating transcription of a regulon involved in attenuating physiological effects of $^1O_2$. This observation suggests that $\sigma^E$ or ChrR can be manipulated to exploit the response of cells and organisms to $^1O_2$. Even though the application refers to observations made in *R. sphaeroides*, the invention is not intended to be limited to this single prokaryote, as responses to $^1O_2$ are present in many other species, including both photosynthetic and non-photosynthetic prokaryotes and eukaryotes.

The observation can be exploited to inhibit or prevent microbial survival, by preventing dissociation between ChrR and $\sigma^E$ or by reducing the extent of dissociation in the microbes. In the presence of $^1O_2$, the microbes would succumb to damage caused by increased oxidative stress.

The observation can alternatively be exploited to increase efficiency of commercial processes for generating commodity chemicals such as, but not limited to, acetic acid and other organic acids, acetone, acrylamide, butanol, ethanol, glycerol, isoprenoids, quinines, and pigments. Nagasawa T & Yamada H, "Microbial production of commodity chemicals," 67 Pure & Appl. Chem. 1241-1256 (1995), incorporated herein by reference as if set forth in its entirety. In particular, photosynthetic organisms for use in such processes can be engineered to inhibit or eliminate binding between ChrR and $\sigma^E$, such that when the microbe finds itself in the presence of $^1O_2$, it readily overcomes any toxic effects by mobilizing its increased available supply of $\sigma^E$ to initiate transcription of the protective regulon, ensuring robust production from the process, notwithstanding the presence of $^1O_2$. Increasing production of these or other commodity chemicals involves inhibiting the interaction between ChrR and $\sigma^E$ in the presence of $^1O_2$ so that the microbe continues to produce a desired commodity chemical notwithstanding oxidative stress. In one approach, the microbe can be engineered either to contain a mutated ChrR that cannot bind $\sigma^E$, or to lack ChrR entirely. A similar effect can be obtained by engineering a microbe for use in the process where the microbe contains a mutated $\sigma^E$ relative to wild-type $\sigma^E$ such that the mutated sigma factor cannot bind ChrR, or binds ChrR only weakly. In some embodiments, the photosynthetic organism is a bacterium, an alga or a plant. In some embodiments, the photosynthetic organism is *R. sphaeroides*. In some embodiments, $\sigma^E$ is modified relative to wild type by engineering a K38E mutation, a K38R mutation or a M42A mutation in $\sigma^E$. In some embodiments, ChrR is modified relative to wild type by engineering a C35S mutation, a C38S mutation, a C38R mutation or a C187/189S in ChrR.

In another aspect, the observation can be exploited by protecting the phototroph from toxic effects of $^1O_2$ by looking beyond the direct interaction of $\sigma^E$ and ChrR, to the genes transcribed directly by $\sigma^E$ or genes whose expression is increased by a $\sigma^E$-dependent transcription factor. For example, where the available supply of $\sigma^E$ is not, or cannot, be increased as noted above, the phototroph, especially a plant, can be engineered to increase expression of genes that encode protective proteins. For example, CfaS, shown herein to be upregulated by $\sigma^E$, encodes cyclopropane-fatty-acyl-phospholipid synthase which catalyzes the generation of cyclopropane fatty acids by adding a methylene bridge across a double bond of a fatty acid. In lipid bilayers, $^1O_2$ can hydroxylate unsaturated fatty acids and membrane-destabilizing lipid peroxides can form. On the other hand, $^1O_2$ cannot hydroxylate cyclopropane fatty acids in the bilayers, so lipid peroxides cannot form and the phototrophs are protected from oxidative stress. Conversely, unwanted or invasive plant species can be made more susceptible to oxidative stress by engineering the phototroph to downregulate genes that encode protective proteins, such as CfaS.

In another aspect, the present invention is summarized in that a consensus promoter responsive to $\sigma^E$ is disclosed as SEQ ID NO:3. In some embodiments, the nucleic acid residues at positions 2, 6, 12, 16, 17 and 20 are G; at position 11 is A; and at positions 19, 22 and 26 are C. The isolated nucleic acid sequence of SEQ ID NO:3 can be operably linked to a heterologous reporter gene or gene of interest to produce a genetic construct suitable for transfer into cells of a phototroph. Expression of the operably linked gene can thereby be placed under the control of $\sigma^E$. In so doing, not only can protective proteins be produced in the presence of $^1O_2$, but any other protein, polypeptide, peptide or oligonucleotide of interest can be induced under such conditions. Similarly, a reporter gene can be provided so that the presence of $^1O_2$ can be detected, observed and monitored.

It is an advantage of the present invention that it provides the skilled person with the tools for efficiently producing products in phototrophic organisms while avoiding long-standing issues arising from the presence of $^1O_2$.

A second advantage is that the methods and compositions are non-toxic to the environment.

These and other features, aspects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

Abbreviations used in the drawings: PS—photosynthetically grown cells, Aero—cells grown by aerobic respiration, WT—wild type, ΔChrR—cells lacking the anti-sigma factor ChrR, Δ$\sigma^E$—cells lacking both $\sigma^E$ and ChrR.

DETAILED DESCRIPTION OF PREFERRED EMBODIMENTS

Figure 1:
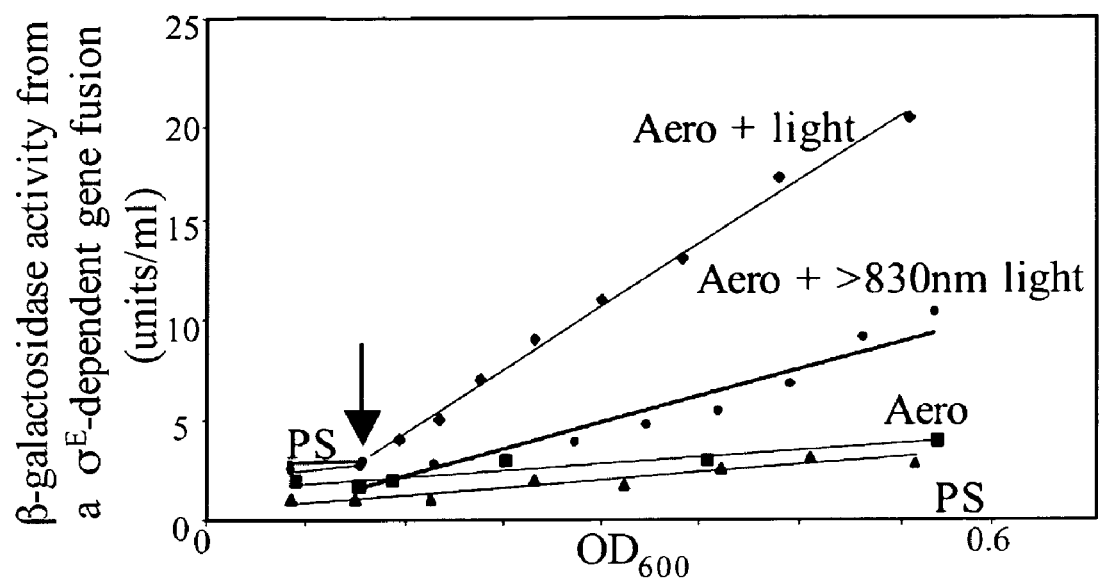
FIG. 1 shows that the conditions that generate $^1O_2$ increase *R. sphaeroides*' $\sigma^E$ activity. Cells were grown in either steady-state cultures or were shifted from photosynthetic to aerobic conditions in the presence of light, which was either white, unfiltered light (light) or filtered light at >830 nm. The arrow indicates the time of shift. β-galactosidase activity from a $\sigma^E$-dependent reporter gene is shown.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

As used herein, a "phototroph" or "photosynthetic organism" refers to any organism that is capable of photosynthesis.

EXAMPLES

Example 1

Role of $\sigma^E$ in Response to $^1O_2$

Methods

Bacterial strains and plasmids: R. sphaeroides 2.4.1 (wild-type, WT), R. sphaeroides with a mutant ChrR (ΔChrR) (chrR-1::drf; see Newman et al., supra.) or R. sphaeroides with both a mutant $\sigma^E$ ($\Delta\sigma^E$) and ΔChrR (TF18; rpoEchrR-1::drf, see Schilke B & Donohue T, "ChrR positively regulates transcription of the Rhodobacter sphaeroides cytochrome $c_2$ gene," J. Bacteriol. 177:1929-1937 (1995), incorporated herein by reference as if set forth in its entirety) were grown at 30° C. in Sistrom's succinate-based minimal medium A. Media used for growth of strains containing low-copy lacZ reporter plasmids was supplemented with 25 µg/ml kanamycin.

Growth conditions: For aerobic respiratory growth, 500 ml of media was bubbled with a mixture of 69% $N_2$, 30% $O_2$ and 1% $CO_2$ in the dark. Conversely, for photosynthetic growth, 500 ml of media was bubbled with a mixture of 95% $N_2$ and 5% $CO_2$ in front of an incandescent light source (10 W/m² as measured with a Yellow-Springs-Kettering model 6.5A radiometer through a Corning 7-69, 620 to 110 nm filter).

To test the effects of $^1O_2$, photosynthetic cultures were exposed to aerobic growth conditions (69% $N_2$, 30% $O_2$ and 1% $CO_2$) in the presence or in the absence of light (10 W/m²). Where indicated, light was passed through a 1283 filter (Kopp Glass; Pittsburgh, Pa.) that impedes >99% of light at wavelengths <770 nm, but transmits >45% of light at 830 nm and >80% of light at 900 nm. When using methylene blue (Sigma-Aldrich; St. Louis, Mo.) to generate $^1O_2$, a final concentration of 1 µM was added to aerobic cultures in the presence or in the absence of incandescent light (10 W/m²). To test the effects of other ROS, 0.5 mM $H_2O_2$, 1 mM diamide or 1 mM paraquat (Sigma-Aldrich) was added to aerobic cultures.

All experiments were initiated when cultures reached ~2×10⁸ cfu/ml to minimize light or $O_2$ limitation to photosynthetic and aerobic cells, respectively. To measure cell viability, samples were removed, diluted and plated in media supplemented with 25 µg/ml kanamycin to select for the rpoE P1::lacZ reporter plasmid. The whole cell abundance of carotenoids was measured as described in Cohen-Bazire G, et al., "Kinetic studies of pigment synthesis by non-sulfur purple bacteria," J. Cell Physiol. 49:25-68 (1957).

Determining promoter activity: Promoter activity was determined by measuring β-galactosidase activity from a low copy rpoE P1::lacZ reporter plasmid or a trxA::lacZ reporter plasmid. The promoter for the thioredoxin gene (trxA, −214 to +27 relative to the known transcription initiation site) was fused to lacZ and mobilized into R. sphaeroides.

β-galactosidase activity (units/ml of culture) was calculated as follows: ($A_{420}$×1000)/(Cell volume in assay (ml)× Time of assay (min)). Culture density was typically monitored by measuring $A_{600}$ in a BioSpec 1601 spectrophotometer (Schimatzu; Columbia, Md.). The density of cultures treated with methylene blue was monitored at 500 nm because methylene blue absorbs light between 609-668 nm. The differential rate of β-galactosidase synthesis was determined by calculating the slope from plots of enzyme activity (units/ml of culture) against optical density. All experiments were repeated a minimum of three times with differential rates of β-galactosidase synthesis typically deviating less than two-fold between experiments.

Identification of $\sigma^E$ target genes: Triplicate cultures of WT and ΔChrR were grown aerobically to ~2-3×10⁸ CFU/ml. RNA was isolated and cDNA was synthesized, labeled and hybridized to R. sphaeroides GeneChip Custom Express microarrays (Affymetrix). After data extraction using Affymetrix MAS 5.0 software, data sets were imported into GeneSpring software (Silicon Genetics; Redwood City, Calif.) for normalization and analysis (Gene Expression Omnibus (GEO) accession number GSE2219).

Candidate $\sigma^E$ promoters (extending ~200 bp upstream of the predicted start of translation, Table 1) were amplified from 20 ng of WT chromosomal DNA in EasyStart PCR tubes (Molecular BioProducts; San Diego, Calif.) with 2.5 units Pfu Turbo (Stratagene; La Jolla, Calif.). PCR products were cloned into a plasmid (pRKK96) containing a known transcriptional terminator for in vitro assays or into a lacZ reporter plasmid (pRKK200) for determining activity in vivo. In vitro transcription assays with reconstituted R. sphaeroides $\sigma^E$ (E$\sigma^E$) were performed with 20 nM of plasmid DNA.

TABLE 1

Genes with RNA expression levels ≧3-fold in ΔChrR strain.[1,2,3]

| ORF | ΔChrR[1] | WT | Fold Increase[2] | Common Name | Description[3] |
|---|---|---|---|---|---|
| RSP0028 | 0.438 | 0.111 | 3.9 | | Putative short-chain dehydrogenase/reductase |
| RSP0103 | 1.451 | 0.376 | 3.9 | nuoE | NADH dehydrogenase (ubiquinone), 24-kDa subunit |
| RSP0105 | 1.525 | 0.131 | 11.7 | nuoG | Respiratory-chain NADH dehydrogenase 75-kDa subunit |
| RSP0107 | 2.148 | 0.523 | 4.1 | nuoI | 7Fe ferredoxin: 3Fe-4S ferredoxin: 4Fe-4S ferredoxin, iron-sulfur-binding domain |
| RSP0136 | 0.378 | 0.103 | 3.7 | | Putative integrase for prophage CP-933U |
| RSP0216 | 0.503 | 0.0602 | 8.4 | | Hypothetical |
| RSP0258 | 48.66 | 14.19 | 3.4 | pufA | LHI α, light-harvesting B875 protein |
| RSP0261 | 1.147 | 0.287 | 4.0 | bchY | Chlorophyllide reductase, BchY subunit |
| RSP0262 | 0.607 | 0.0783 | 7.7 | bchX | Chlorophyllide reductase, BchX subunit |
| RSP0286 | 2.301 | 0.489 | 4.7 | bchB | Light-independent protochlorophyllide reductase |
| RSP0287 | 1.068 | 0.203 | 5.3 | bchH | Magnesium-chelatase subunit H |
| RSP0288 | 3.402 | 1.012 | 3.4 | bchL | Light-independent protochlorophyllide reductase iron protein |
| RSP0300 | 0.328 | 0.106 | 3.1 | | ABC branched chain amino acid transporter, inner membrane subunit |
| RSP0351 | 2.035 | 0.0421 | 48.3 | | Pseudogene of D-threo-aldose 1-dehydrogenase |
| RSP0464 | 0.348 | 0.0957 | 3.6 | | Putative protease |
| RSP0473 | 0.47 | 0.149 | 3.2 | | Phospholipase-D family protein |
| RSP0483 | 0.483 | 0.16 | 3.0 | | |
| RSP0601 | 20.71 | 0.541 | 38.3 | rpoH2 | RNA polymerase σ factor RpoH2 (σ-32 group, heat shock) |
| RSP0770 | 0.173 | 0.0524 | 3.3 | | |
| RSP0799 | 7.747 | 2.212 | 3.5 | | Conserved hypothetical protein |
| RSP0820 | 0.817 | 0.201 | 4.1 | | Putative cytochrome B561 |
| RSP0947 | 0.432 | 0.129 | 3.4 | | Hypothetical protein |
| RSP1008 | 0.501 | 0.132 | 3.8 | | |
| RSP1025 | 4.55 | 1.287 | 3.5 | | Conserved hypothetical protein |
| RSP1026 | 2.13 | 0.65 | 3.3 | | |
| RSP1087 | 8.799 | 1.865 | 4.7 | | Short-chain dehydrogenase/reductase family member |
| RSP1088 | 7.219 | 0.338 | 21.4 | | Hypothetical protein |
| RSP1089 | 4.204 | 0.573 | 7.3 | | Sugar/cation symporter, GPH family |
| RSP1090 | 5.57 | 0.0311 | 179.3 | | Putative cyclopropane/cyclopropene fatty acid synthesis protein |
| RSP1091 | 31.93 | 1.968 | 16.2 | | Putative cyclopropane/cyclopropene fatty acid synthesis protein, flavin amine oxidase |
| RSP1092 | 17.55 | 1.399 | 12.5 | rpoE | RNA polymerase σ factor RpoE (ECF group, extracytoplasmic function) |
| RSP1263 | 0.273 | 0.0749 | 3.6 | | |
| RSP1409 | 48.75 | 0.302 | 161.6 | | Beta-Ig-H3/fasciclin domain |
| RSP1410 | 2.606 | 0.709 | 3.7 | | Conserved hypothetical protein |
| RSP1504 | 0.481 | 0.056 | 8.6 | | Conserved hypothetical protein |
| RSP1540 | 0.973 | 0.297 | 3.3 | | Predicted secreted hydrolase |
| RSP1546 | 16.61 | 3.279 | 5.1 | bfr | Bacterioferritin |
| RSP1591 | 4.283 | 0.675 | 6.3 | | Predicted glutathione S-transferase, C-terminal |
| RSP1619 | 0.265 | 0.0271 | 9.8 | | Hypothetical |
| RSP1656 | 0.123 | 0.0269 | 4.6 | | Hypothetical |
| RSP1759 | 8.572 | 2.632 | 3.3 | | Hypothetical |
| RSP1760 | 6.211 | 1.166 | 5.3 | | Hypothetical protein |
| RSP1852 | 19.85 | 1.922 | 10.3 | | Conserved hypothetical protein |
| RSP1853 | 1.235 | 0.183 | 6.8 | TrkH2 | Potassium uptake transporter, transmembrane component, TrkH |
| RSP1895 | 1.454 | 0.145 | 10.1 | | Small-conductance mechanosensitive ion channel |
| RSP1924 | 0.341 | 0.1 | 3.4 | | Probable biotin synthase |
| RSP2030 | 0.294 | 0.0458 | 6.4 | | Putative sensor histidine kinase (fragment) |
| RSP2037 | 0.619 | 0.191 | 3.2 | | Conserved hypothetical protein |

TABLE 1-continued

Genes with RNA expression levels ≧3-fold in ΔChrR strain.[1,2,3]

| ORF | ΔChrR[1] | WT | Fold Increase[2] | Common Name | Description[3] |
|---|---|---|---|---|---|
| RSP2066 | 0.908 | 0.13 | 7.0 | | Hypothetical |
| RSP2143 | 5.775 | 1.315 | 4.4 | | DNA photolyase, cryptochrome 1 apoprotein (blue-light photoreceptor) |
| RSP2144 | 11.1 | 1.123 | 9.9 | cfaS | Cyclopropane-fatty-acyl-phospholipid synthase (CfaS) |
| RSP2145 | 5.831 | 1.483 | 3.9 | trgA | Tellurite resistance protein |
| RSP2235 | 0.393 | 0.0335 | 11.7 | | Conserved hypothetical protein |
| RSP2268 | 4.223 | 0.991 | 4.3 | | Metallo β lactamase superfamily |
| RSP2294 | 2.737 | 0.896 | 3.1 | gloB | Putative hydroxyacylglutathione hydrolase (glyoxalase II) (GLX II) protein hydroxyacylgluta |
| RSP2314 | 4.134 | 1.12 | 3.7 | | Oxidoreductase - Aldo/keto reductase family: chromogranin/secretogranin |
| RSP2315 | 3.96 | 1.056 | 3.8 | | Conserved hypothetical protein |
| RSP2381 | 0.258 | 0.0597 | 4.3 | | Putative 3-methyladenine DNA glycosylase |
| RSP2389 | 2.144 | 0.0744 | 28.8 | | Putative glutathione peroxidase |
| RSP2390 | 1.758 | 0.391 | 4.5 | acuC1 | Putative acetoin utilization protein |
| RSP2391 | 0.469 | 0.0957 | 4.9 | | Putative ABC transporter (permease) |

[1]ΔChrR: *R. sphaeroides* WT with trimethoprim cartridge inserted into ChrR.
[2]Increase in RNA abundance from comparing transcript levels in WT and ΔChrR cells. Data has been deposited at GEO under accession number GSE2219.
[3]Function known or predicted by genome annotation.

Results

Conditions that generate $^1O_2$ within the photosynthetic apparatus increase *R. sphaeroides* $\sigma^E$ activity: Mutations that inactivate an early enzyme in carotenoid biosynthesis, CrtB, cause a small increase in $\sigma^E$ activity (data not shown). Since carotenoids play a protective role against $^1O_2$, it was determined whether $^1O_2$ directly affected $\sigma^E$ activity.

To determine if *R. sphaeroides* $\sigma^E$ activity responds to $^1O_2$, we examined the differential rate of β-galactosidase synthesis from a $\sigma^E$-dependent rpoE P1::lacZ reporter fusion after anaerobic, photosynthetic cells were exposed to $O_2$ in the presence of light. After exposure to $O_2$, the cells maintain approximately the same doubling rate, since $O_2$ is used as a respiratory electron acceptor. However, after exposure to $O_2$, the differential rate of β-galactosidase synthesis from the $\sigma^E$-dependent promoter increased ~10-fold (from 6 to 65) when compared to a control culture grown under either a steady state photosynthetic condition (light in the absence of $O_2$) or a respiring condition (30% $O_2$) (FIG. 1 and Table 2).

TABLE 2

Differential rates of β-galactosidase synthesis from the $\sigma^E$-dependent rpoE P1::lacZ reporter under conditions that either do (+) or do not (−) generate $^1O_2$.[1,2]

| Strain | Growth | $^1O_2$ | Rate |
|---|---|---|---|
| WT | PS | − | 6 |
| WT | Aero | − | 8 |
| WT | PS → Aero + light | + | 65 |
| WT | PS → Aero (dark) | − | 8 |
| WT | PS (>830 nm) | − | 2 |
| WT | PS → Aero (>830 nm) | + | 35 |

[1]Aero = cells grown by aerobic respiration (30% $O_2$),
[2]PS = cells grown photosynthetically.

This transcriptional response was maintained throughout the experiment, suggesting that $\sigma^E$ activity was sustained. There was less than a two-fold increase in the differential rate of β-galactosidase synthesis from the rpoE P1::lacZ reporter fusion when photosynthetic cells were shifted to aerobic conditions in the dark (Table 2). This was expected since little $^1O_2$ is made under this condition due to lack of light needed to produce triplet state chlorophyll molecules. From these results, one can conclude that the combination of light and $O_2$, conditions known to generate $^1O_2$ within the photosynthetic apparatus, are required for this transcriptional response.

Control experiments indicated that this response was dependent on $\sigma^E$ since the differential rate of a β-galactosidase synthesis from the rpoE P1::lacZ reporter fusion in $\Delta\sigma^E$ cells (<1 unit) did not increase upon exposure to $^1O_2$. $\Delta\sigma^E$ cells grow under these conditions, presumably because the carotenoids within the photosynthetic apparatus quench $^1O_2$. In addition, it appears that $^1O_2$ does not fully induce $\sigma^E$ activity since the differential rate of β-galactosidase synthesis from the rpoE P1::lacZ reporter fusion in WT cells exposed to $^1O_2$ was 10-fold less than that seen in ΔChrR cells (65 versus 650).

Wavelengths of light that excite chlorophyll pigments are sufficient to increase $\sigma^E$ activity: If production of $^1O_2$ by the photosynthetic apparatus was responsible for this transcriptional response, then wavelengths of light known to generate triplet state chlorophyll molecules within the light harvesting complexes should increase $\sigma^E$ activity. *R. sphaeroides* contains two light harvesting complexes, B800-850 and B875, named for their absorption maxima in the near infrared. To determine if light absorbed by the light harvesting complexes could cause this response, we looked at the action spectrum of this transcriptional response. Under photosynthetic conditions with light that was filtered to remove wavelengths <830 nm, the differential rate of β-galactosidase synthesis from the $\sigma^E$-dependent promoter was an ~4-fold lower than that observed with cells grown in white light (Table 2), presumably because the cells grow slower when light <830 nm is removed. However, there was an ~17-fold increase in the differential rate of β-galactosidase synthesis when cultures illuminated with >830 nm light were exposed to $O_2$ (Table 2). The magnitude of this response was similar to that observed when photosynthetic cells were exposed to $O_2$ and white light (~17-fold versus ~10-fold, Table 2). Thus, wavelengths of light that excite the light harvesting complexes are sufficient to increase $\sigma^E$ activity.

Figure 2:
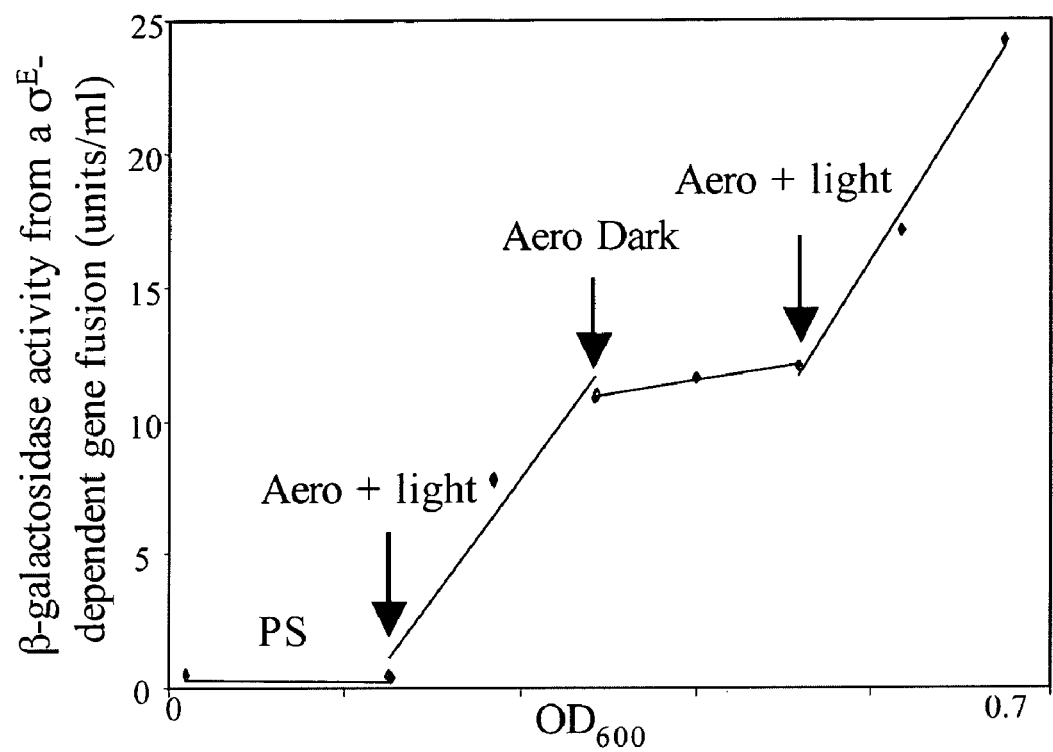
FIG. 2 shows that cells require continued exposure to $^1O_2$ to maintain increased $\sigma^E$ activity. β-galactosidase activity from a $\sigma^E$-dependent reporter gene when photosynthetically grown cells are shifted to aerobic conditions in the presence or absence of light. Arrows indicate each shift.

Continued exposure to conditions that generate $^1O_2$ in the photosynthetic apparatus are needed to sustain this response: The half-life of $^1O_2$ in cells is less than 100 ns and was used to further test if $\sigma^E$ activity was responding to $^1O_2$. For example, if increased $\sigma^E$ activity required $^1O_2$, then placing photosynthetic cells that had previously been exposed to $O_2$ in the dark should terminate this transcriptional response. When the cells were shifted to aerobic conditions in the presence of light, we observed an expected increase in the differential rate of β-galactosidase synthesis from the $\sigma^E$-dependent promoter (~10-fold, FIG. 2 and Table 3). However, when these cells were placed in the dark (i.e., conditions that allow growth via respiration but prevent $^1O_2$ formation), the differential rate of β-galactosidase synthesis decreased ~9-fold (FIG. 2 and Table 3). Further, an ~8-fold increase in the differential rate of β-galactosidase synthesis from the $\sigma^E$-dependent promoter was observed when the same cells were placed back into the light to restore $^1O_2$ formation (FIG. 2 and Table 3). This suggests a reversible transcriptional response to $^1O_2$ and that increased $\sigma^E$ activity requires continued exposure to $^1O_2$.

TABLE 3

Continued exposure to $^1O_2$ is required for increased $\sigma^E$ activity.

| Growth | $^1O_2$ | Rate |
|---|---|---|
| PS | − | 7 |
| Aero + Light | + | 73 |
| Aero + Dark | − | 8 |
| Aero + Light | + | 63 |

*R. sphaeroides* $\sigma^E$ activity is increased by formation of $^1O_2$ in the absence of the photosynthetic apparatus: If $^1O_2$ was responsible for the observed $\sigma^E$ transcriptional response, then other conditions that generate this ROS should also increase $\sigma^E$ activity. To test this hypothesis, one can generate $^1O_2$ by illumination of methylene blue in the presence of $O_2$ to produce a similar response. When aerobically grown WT cells were exposed to 1 μM methylene blue in the presence of light and $O_2$, cell growth continued and the differential rate of β-galactosidase synthesis from the rpoE P1::lacZ reporter fusion increased ~20-fold compared to aerobic cells grown in the absence of methylene blue (Table 4). Control experiments indicated there was less then a two-fold increase in the rate of β-galactosidase synthesis when aerobic cultures were exposed to methylene blue in the dark (Table 4). The lack of a comparable increase in $\sigma^E$ activity in aerobic cells exposed to methylene blue in the dark is expected since both light and $O_2$ are required for this compound to generate $^1O_2$.

TABLE 4

Light plus methylene blue increases $\sigma^E$ activity.[1]

| Strain | Growth | $^1O_2$ | Rate |
|---|---|---|---|
| WT | Aero | − | 5 |
| WT | Aero + light | − | 8 |
| WT | Aero + methylene blue + light | + | 151 |
| WT | Aero + methylene blue (dark) | − | 8 |

[1]Differential rates of β-galactosidase synthesis from the $\sigma^E$-dependent rpoE::lacZ fusion when WT cells are grown aerobically under conditions that either do or do not generate $^1O_2$.

For these experiments, cells were grown in the presence of 30% $O_2$, a condition where pigment-protein complexes of the photosynthetic apparatus are not detectable. Therefore, the transcriptional response to $^1O_2$ can occur in cells that either contain or lack the photosynthetic apparatus.

Other ROS do not produce a similar increase in $\sigma^E$ activity: The damaging effects of $^1O_2$ on many biomolecules could stimulate the formation of other ROS. To test if other ROS could produce an increase in $\sigma^E$ activity, the differential rate of β-galactosidase synthesis from a rpoE P1::lacZ reporter fusion was monitored in aerobic cells treated with concentrations of hydrogen peroxide ($H_2O_2$), paraquat (to stimulate superoxide ($O_2^-$) formation) or diamide (to alter the oxidation-reduction state of the cytoplasmic thiol pool), previously shown to generate an oxidative stress response in *R. sphaeroides*. Li K, et al., "Expression of the trxA gene for thioredoxin 1 in *Rhodobacter sphaeroides* during oxidative stress," Arch. Microbiol. 180:484-489 (2003). For these experiments, the differential rate of β-galactosidase synthesis was monitored from a control trxA::lacZ reporter fusion, since the trx promoter has previously been shown to respond to oxidative stress in *R. sphaeroides*.

The addition of paraquat or $H_2O_2$ to aerobic cells produced increases in the differential rate of β-galactosidase synthesis from the trxA::lacZ reporter gene that are consistent with changes in abundance of trxA transcripts produced by these compounds in previous studies (Table 5). However, the differential rate of β-galactosidase synthesis from the $\sigma^E$-dependent reporter fusion either decreased (paraquat) or increased no more than 1.2-fold ($H_2O_2$) when compared to untreated cells (Table 5). Any observed increase in $\sigma^E$ activity in the presence of these ROS was below the 10-fold increase in $\sigma^E$ activity seen when cells are exposed to $^1O_2$.

TABLE 5

Other ROS do not increase $\sigma^E$ activity.[1]

| Addition | ROS | rpoE P1::lacZ fusion | trxA::lacZ fusion |
|---|---|---|---|
| None | — | 11 | 185 |
| Paraquat | superoxide | 6 | 450 |
| $H_2O_2$ | peroxide | 13 | 220 |
| Diamide | oxidizes cysteine thiols | 3 | ND |

[1]Differential rates of β-galactosidase synthesis from the indicated promoters when WT cells are grown aerobically under conditions that either do or do not generate indicated ROS.
ND—Not Determined.

$\sigma^E$ activity in the presence of diamide was not monitored because previous work has shown that $\sigma^E$ activity does not increase upon exposure to this compound. Based on these results, the transcriptional response observed when $^1O_2$ is generated does not occur in the presence of other ROS.

When carotenoids are low, cells require $\sigma^E$ to mount response to $^1O_2$: While cells Δ$\sigma^E$ cells are unable to mount this transcriptional response to $^1O_2$ (FIG. 1 and Table 2), exponential growth of a Δ$\sigma^E$ strain continues when a photosynthetic culture is shifted to aerobic conditions in the presence of light (data not shown). This occurs presumably because carotenoids within the photosynthetic apparatus quench $^1O_2$. To assess the relative importance of carotenoids and $\sigma^E$ in the presence of $^1O_2$, we monitored growth of cells containing low levels of carotenoids in the presence and absence of $\sigma^E$. For this analysis, cells were grown by aerobic respiration (30% $O_2$) since they have 20-fold less total carotenoids than photosynthetic cells grown at 10 W/m² (~10 μg carotenoid/2×10¹⁰ cells compared to ~200 μg carotenoid/2× 10¹⁰ cells, respectively). The use of aerobically grown cells is preferable to studying a carotenoid-minus Δ$\sigma^E$ mutant because the lack of carotenoids in such a mutant lowers photosynthetic growth rates.

Figure 3:
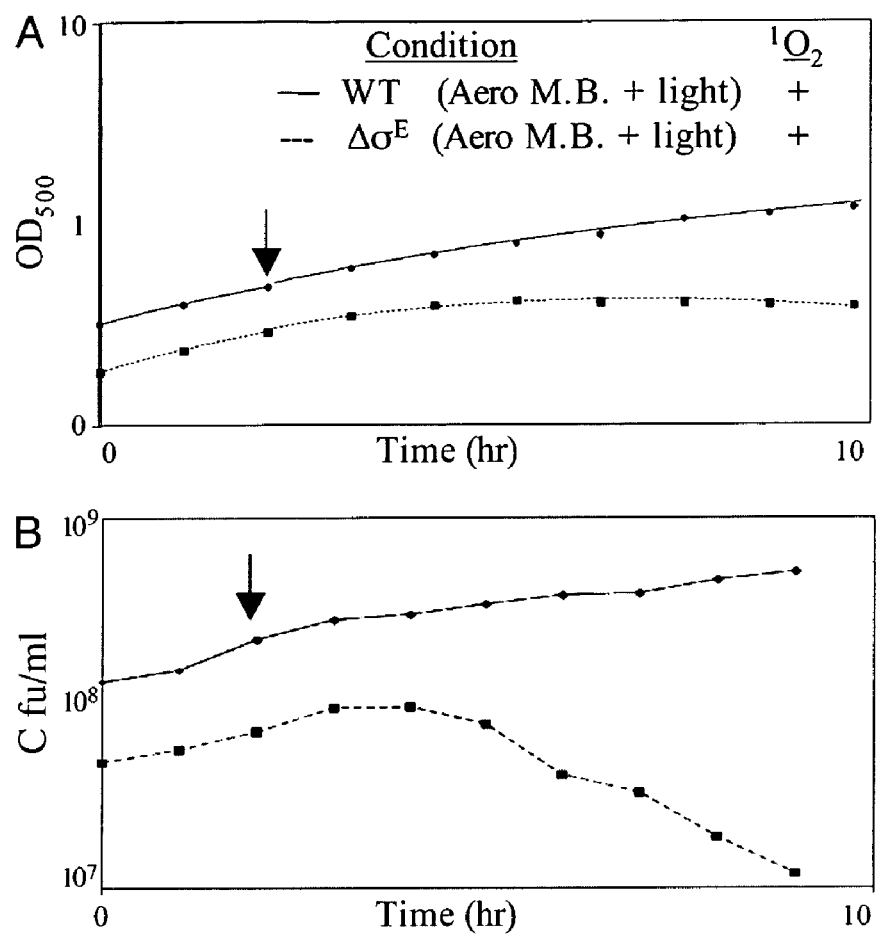
FIG. 3 shows that $^1O_2$ is bacteriocidal to a $\Delta\sigma^E$ mutant when carotenoids are low. Aerobically grown wild type or $\Delta\sigma^E$ cells were treated with methylene blue in the presence of light. The arrow indicates when methylene blue and light were added. (A) Optical density measurements ($OD_{500nm}$) and (B) viable plate counts (cfu/ml).

Exponential growth of aerobically grown WT cells continued after exposure to $^1O_2$ (FIG. 3A). In contrast, the number of colony forming units per ml (cfu/ml) of the Δσ$^E$ mutant culture decreased ~10-fold after 8 hours of exposure to $^1O_2$ (FIG. 3B). The bacteriocidal effect of $^1O_2$ on the Δσ$^E$ mutant when carotenoid levels are low shows that both sigma factor activity and carotenoids are critical to viability in the presence of this $^1O_2$.

Additional members of the σ$^E$ regulon: To identify genes that are part of this transcriptional response to $^1O_2$, we compared RNA levels in aerobically grown (30% $O_2$) WT cells and in a ΔChrR mutant. Because ChrR inhibits σ$^E$ activity, one looks for RNA that is more abundant in the ΔChrR mutant. As expected, global gene expression analysis showed an increase (~12-fold) in rpoE-specific RNA from ΔChrR cells.

RNA from ~180 genes (~60 operons) was >3-fold more abundant in cells that contained increased σ$^E$ activity (Table 1). In contrast, the ~35-fold increase in cycA P3 activity that occurs in ΔChrR cells in vivo causes only an ~1.6-fold increase in total cycA-specific RNA (Table 1). The smaller increase in cycA-specific RNA levels reflects the fact that cycA contains additional strong promoters that are recognized by other sigma factors. This suggests that a global gene expression microarray approach might miss other σ$^E$-dependent genes that also contain multiple promoters.

Figure 4:
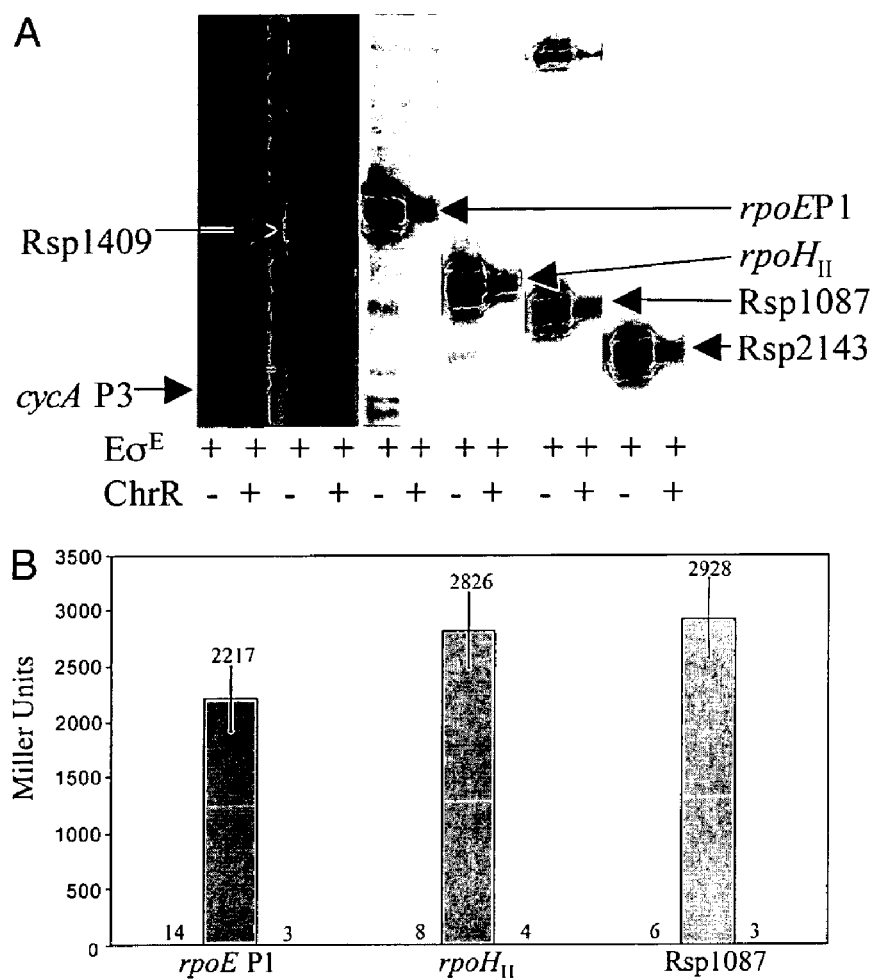
FIG. 4 identifies additional $\sigma^E$-dependent promoters. (A) Products of in vitro transcription reactions using reconstituted R. sphaeroides ($E\sigma^E$) and the indicated potential promoter. As an additional control to demonstrate the $\sigma^E$-dependence of these transcripts, ChrR was added to indicated reactions. Note that the first four lanes were exposed to a phosphoscreen twice as long as the remainder of the gel to detect low abundance transcripts from the cycA P3 and Rsp1409 promoters. Experiments were repeated at least three times, with a representative gel shown. The $\sigma^E$-dependent transcripts appear as two products due to termination at different bases within the SpoT 40 transcriptional terminator on the template used. (B) Activity of selected $\sigma^E$-dependent promoters in R. sphaeroides. Shown are β-galactosidase levels (in Miller units) from the indicated promoter fused to lacZ in wild type cells (■), ΔChrR cells (□), or both $\Delta\sigma^E$ and ΔChrR cells (□). All assays were performed in triplicate, with bars denoting the standard deviation from the mean.
Figure 5:
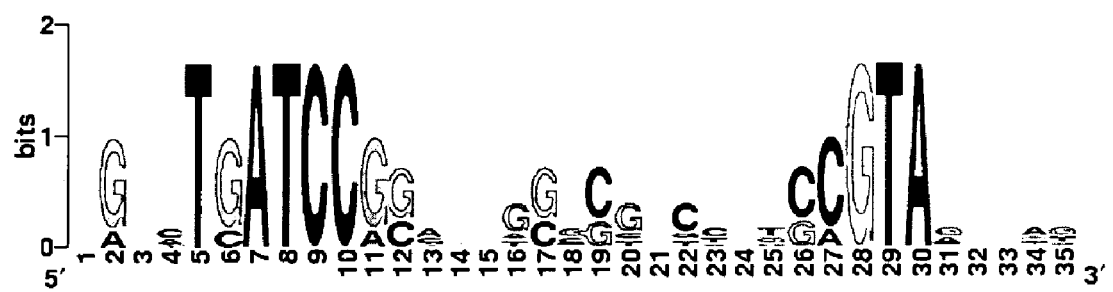
FIG. 5 shows a consensus R. sphaeroides $\sigma^E$ promoter sequence (SEQ ID NO:3) generated from the six known $\sigma^E$-dependent promoters using a position weighted matrix and the WCONSENSUS algorithm (an alignment program by Gary Stormo's laboratory, available at the Washington University School of Medicine website on the world-wide-web; see also Hertz G & Stormo G, "Identifying DNA and protein patterns with statistically significant alignments of multiple sequences," Bioinformatics 15:563-577(1999)).

To test if any of these candidate operons contained a σ$^E$-dependent promoter, we tested DNA upstream of the first gene in each of twenty-eight potential operons for transcription by Eσ$^E$. (Table 6) These operons were chosen either because of their increased levels of expression in cells with elevated σ$^E$ activity or because of a potential role of their gene products in the photosynthetic apparatus (a source of $^1O_2$). It was observed that rpoH$_{II}$, which encodes one of two R. sphaeroides heat shock sigma factors (Rsp0601), is transcribed by σ$^E$. Production of the rpoH$_{II}$ transcript is inhibited by addition of ChrR, as is the case with other σ$^E$-dependent promoters like rpoE P1 and cycA P3 (FIG. 4A). By these criteria, σ$^E$-dependent promoters are also located upstream of Rsp1087 (which may contain two promoters because different sized σ$^E$ transcripts are seen), Rsp1409, and Rsp2143 (FIG. 4A).

TABLE 6

Operons tested for σ$^E$-dependence.

| ORF | Description[1] | Fold increase[2] | Region tested[3] | σ$^E$ promoter[4] | Putative σ$^E$-dependent promoter sequence[4] |
|---|---|---|---|---|---|
| Rsp0106–0114 | NADH: ubiquinone dehydrogenase | 1.7–4.1 | −230 to +1 | − | |
| Rsp0255–0261 | Bacteriochlorophyll synthesis, puf | 1.6–4.1 | −221 to +1 | − | |
| Rsp0262–0263 | Bacteriochlorophyll synthesis | 2–7.8 | −232 to +1 | − | |
| Rsp0264–0265 | Carotenoid biosynthesis | 1.4 | −240 to +1 | − | |
| Rsp0269–0271 | Carotenoid biosynthesis, tspO | 1.4–2 | −217 to +1 | − | |
| Rsp0284–0295 | Chlorophyll synthesis, puhA | 1.3–4.7 | −201 to +1 | − | |
| Rsp0296 | Cytochrome c$_2$, cycA | 1.6 | −105 to −42 | + | -88TGATCCN$_{18}$TAGTGA (SEQ ID NO: 4) |
| Rsp0317 | Coproporphyrinogen III oxidase | 1.5 | −195 to +1 | − | |
| Rsp0600–0601 | Heat-shock σ factor, rpoH$_{II}$ | 2.6–38.3 | −209 to −6 | + | -66TGATCCN$_{18}$TAGTAA (SEQ ID NO: 5) |
| Rsp0896–0898 | Putative glutathione S-transferase | 1–2.9 | −225 to +1 | − | |
| Rsp1025–1028 | DNA polymerase I | 1.2–3.6 | −206 to −4 | − | |
| Rsp1087–1091 | Amine oxidoreductase, dehydrogenase | 4.7–180 | −203 to +1 | + | -54TGATCCN$_{18}$TATCTG (SEQ ID NO: 6) |
| Rsp1092–1093 | RpoEchrR[5] | 12.6 | −132 to −77 | + | -130TGATCCN$_{18}$TAAGAA (SEQ ID NO: 7) |
| Rsp1175 | Methyltransferase | 1.3 | −219 to +1 | − | |
| Rsp1277–1280 | CbbXYZ | 1.1–2 | −232 to +1 | − | |
| Rsp1409 | TspO-like regulator | 162 | −223 to +1 | + | -70TCATCCN$_{19}$TAGCCT (SEQ ID NO: 8) |
| Rsp1410–1411 | Putative oxidoreductase | 1.6–3.7 | −250 to +1 | − | |
| Rsp1520 | Histidine sensor kinase, prrB | NC | −205 to −6 | − | |
| Rsp1591 | Predicted glutathione S-transferase | 6.4 | −257 to +1 | − | |
| Rsp2143–2146 | DNA photoylase, CP-FA synthetase | 2.3–9.9 | −201 to −2 | + | -49TGATCCN$_{18}$TAAGAG (SEQ ID NO: 9) |
| Rsp2163 | Putative transglycosylase | 1.8 | −406 to −195 | − | |
| Rsp2389–2391 | Putative glutathione oxidase, histone deacytlase | 4.5–28.9 | −189 to +1 | − | |
| Rsp2683–2685 | Cytochrome biogenesis, endonuclease | 1.2 | −206 to +1 | − | |

TABLE 6-continued

Operons tested for $\sigma^E$-dependence.

| ORF | Description[1] | Fold increase[2] | Region tested[3] | $\sigma^E$ promoter[4] | Putative $\sigma^E$-dependent promoter sequence[4] |
|---|---|---|---|---|---|
| Rsp2707–2710 | Pyrophosphate synthase, Zn-dependent protease | 1.9 | −206 to +1 | − | |
| Rsp3075–3076 | Uncharacterized conserved proteins | 11–16.6 | −185 to +1 | − | |
| Rsp3117 | Hypothetical protein | NC | −189 to +1 | − | |
| Rsp3162–3164 | Probable oxidoreductase | 3.7–20.3 | −237 to +1 | − | |
| Rsp3210, 3212 | Quinol oxidase, qxtAB | 6–7.6 | −195 to +1 | − | |
| Rsp3272–3274 | ATP transporter, glutathione degradation | 3.1–12.2 | −212 to +1 | − | |
| Rsp3310 | Short-chain dehydrogenase | 9.1 | −199 to +1 | − | |

[1]Function known or predicted by genome annotation. Genes were chosen based on increased RNA abundance in cells that have elevated $\sigma^E$ activity or for their known role in photosynthetic growth.
[2]Increase in RNA abundance from comparing transcript levels in WT and ΔChrR cells. Data has been deposited at GEO under accession number GSE2219. NC—no change.
[3]Coordinates are numbered relative to the start site of translation.
[4]Based on the ability to detect a $\sigma^E$-dependent transcript in vitro (see FIG. 4A).

Each gene is predicted to be part of a polycistronic operon that encodes uncharacterized proteins. The level of transcripts produced from the rpoH$_{II}$, Rsp1087 and Rsp2143 promoters are comparable to that of rpoE P1 (within 1.1-fold), suggesting that these 4 promoters are of similar strength. In contrast, the abundance of the $\sigma^E$-dependent transcript produced by Rsp1409 in vitro is comparable to the $\sigma^E$-dependent promoter, cycA P3, which has ~80-fold less activity than rpoE P1.

The same putative rpoH$_{II}$ and Rsp1087 promoter regions were fused to lacZ to test for $\sigma^E$-dependent activity in vivo. Expression was not detectable from these reporter fusions in WT R. sphaeroides cells, but it was comparable to that of rpoE P1 in ΔChrR cells (FIG. 4B). In addition, activity from the rpoH$_{II}$ and Rsp1087 promoters was not detectable in Δ$\sigma^E$ cells (FIG. 4B). This suggests that transcription from this promoter region is dependent solely on $\sigma^E$, as is the case for rpoE P1.

Example 2

Inhibiting a Microbial $^1O_2$ Response

Generation of ChrR mutants to irreversibly bind to $\sigma^E$: The N-terminal anti-sigma domain of ChrR (ChrR-ASD) appears important in binding between ChrR and $\sigma^E$ (data not shown). The skilled artisan is familiar with methods for delivering genetically engineered antimicrobial agents to microbes by phage therapy. Westwater C, et al., "Use of genetically engineered phage to deliver antimicrobial agents to bacteria: an alternative therapy for treatment of bacterial infections," Antimicrob. Agents Chemother. 47:1301-1307 (2003), incorporated herein as if set forth in its entirety. Phage delivery systems are advantageous because they allow for targeting specific bacterial cells at a high frequency. Accordingly, a phage DNA is modified to contain a coding sequence that codes for at least amino acids 1-85 from GenBank Accession No. AAB 17905 (SEQ ID NO:1), which discloses the R. sphaeroides full-length ChrR sequence. The N-terminal portion of ChrR encoded by this construct is sufficient to irreversibly bind zinc and $\sigma^E$. However, cells containing this or similar N-terminal ChrR variants are not able to mount a response to $^1O_2$, resulting in a condition where cells have increased sensitivity to this reactive oxygen species.

Bacterial cells are grown under standard culture conditions. Once an adequate concentration of bacterial cells are present, they are infected with a phage modified to express at least amino acids 1-85 of SEQ ID NO:1. Following exposure to the phage, oxidative stress ensues, but the cells do not express genes regulated by $\sigma^E$. Consequently, the concentration of bacterial cells decreases.

Alternatively, bacterial cells are infected with a phage modified to express at least amino acids 1-85 of SEQ ID NO:1. They are then grown under standard culture conditions; however, the concentration of bacterial cells does not increase upon oxidative stress because the cells do not express genes regulated by $\sigma^E$.

Other methods for reducing availability of $\sigma^E$ can include using RNAi directed against $\sigma^E$, mutating the promoter that directs transcription of $\sigma^E$ (see Newman et al. (1999), supra), and engineering the cells to put $\sigma^E$ under control of a regulatable promoter or repressor.

Example 3

Generating Commodity Chemicals in Phototrophs in the Presence of $^1O_2$

Bacterial cells with a modified ChrR that cannot bind $\sigma^E$ are grown under standard culture conditions. However, growth and consequently production of a commodity chemical are increased because the cells are protected against the deleterious effects of $^1O_2$.

Likewise, bacterial cells with a modified $\sigma^E$ that cannot be bound by ChrR are grown under standard culture conditions. However, growth and consequently production of a commodity chemical are increased because the cells are protected against the deleterious effects of $^1O_2$.

Example 4

Modifying Plants Lipid Bilayers for Protection During $^1O_2$ Challenge

Methods of manipulating plant genes are known to the skilled artisan. For example, Constabel C, et al., "Transgenic potato plants overexpressing the pathogenesis-related STH-2 gene show unaltered susceptibility to *Phytophthora infestans* and potato virus X," Plant Mol. Biol. 22:775-782 (1993), incorporated herein by reference as if set forth in its entirety. Accordingly, a plant is modified such that the plant exhibits a high level of cyclopropane-fatty-acyl-phospholipid synthase (CfaS) relative to an unmodified plant. The plant is grown under standard conditions; however, growth is increased because the plant is protected against the deleterious effects of $^1O_2$.

Example 5

Producing Peptides in Phototrophs During $^1O_2$ Challenge

Methods of inserting a gene of interest into a plasmid are known to the skilled artisan. Schilke & Donohue, supra. A gene encoding a product of interest is inserted into a plasmid under regulation of a $\sigma^E$-dependent promoter selected from the consensus sequence (SEQ ID NO:3) in FIG. 5. Bacterial cells containing a plasmid having a gene regulated by a $\sigma^E$-dependent promoter selected from the consensus sequence (SEQ ID NO:3) in FIG. 5 are grown under standard culture conditions. However, cell growth and production of the gene product are increased because $^1O_2$ increases transcription from the promoter.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method for protecting *Rhodobacter sphaeroides* cells from damage in the presence of singlet oxygen, the method comprising the steps of:
providing in the cells a $\sigma^E$ and a $\sigma^E$-binding anti-sigma agent to obtain treated cells, at least one of the $\sigma^E$ and the anti-sigma agent being encoded by a non-native form of SEQ ID NO:2 and SEQ ID NO:1, respectively, that reduces binding between the $\sigma^E$ and the anti-sigma agent, the non-native form of $\sigma^E$ comprising a mutation selected from the group consisting of K38E, K38R, and M42A, the non-native form of the anti-sigma agent comprising a mutation selected from the group consisting of H6A, H31A, C35A, C35S, C38A, C38S, C38R and C187/189S, thereby protecting the treated cells from damage in the presence of singlet oxygen; and
measuring protection of the treated cells from damage in the presence of singlet oxygen, wherein the protection is greater in the treated cells than in *Rhodobacter sphaeroides* cells in which binding between $\sigma^E$ and the anti-sigma agent is not reduced.

2. A method for protecting *Rhodobacter sphaeroides* cells that natively comprise a $\sigma^E$ and a $\sigma^E$-binding anti-sigma agent from damage in the presence of singlet oxygen, the method comprising the step of:
eliminating the anti-sigma agent from the cells to produce cells that lack the anti-sigma agent, thereby protecting the cells obtained in the eliminating step from damage in the presence of singlet oxygen; and measuring protection of the cells obtained in the eliminating step from damage in the presence of singlet oxygen, wherein the protection is greater in the cells obtained in the eliminating step than in *Rhodobacter sphaeroides* cells that natively comprise a $\sigma^E$ and a $\sigma^E$-binding anti-sigma agent in which binding between $\sigma^E$ and the anti-sigma agent is not reduced.

3. A method for protecting *Rhodobacter sphaeroides* cells from damage in the presence of singlet oxygen, the method comprising the steps of:
providing in the cells at least one of a $\sigma^E$ and a $\sigma^E$-binding anti-sigma agent encoded by a non-native form of SEQ ID NO:2 and SEQ ID NO:1, respectively, that reduces binding between the $\sigma^E$ and the anti-sigma agent, the non-native form of the $\sigma^E$ comprising at least one mutation selected from the group consisting of K38E, K38R, and M42A, the non-native form of the anti-sigma agent comprising at least one mutation selected from the group consisting of H6A, H31A, C35A, C35S, C38A, C38S, C38R and C187/189S, wherein the providing step comprises the step of introducing into SEQ ID NO:2 the at least one $\sigma^E$ mutation, thereby protecting the cells from damage in the presence of singlet oxygen.

4. A method as recited in claim 3, wherein the providing step comprises the step of introducing into SEQ ID NO:1 the at least one anti-sigma agent mutation.

5. A method as recited in claim 3, wherein the cells produce a commodity chemical product.

6. A method as recited in claim 3, wherein the commodity product is selected from the group consisting of acetic acid, acetone, acrylamide, butanol, ethanol, glycerol, hydrogen peroxide and lactic acid.

7. A method for protecting *Rhodobacter sphaeroides* cells from damage in the presence of singlet oxygen, the method comprising the steps of:
providing in the cells at least one of a $\sigma^E$ and a $\sigma^E$-binding anti-sigma agent to obtain treated cells, wherein the at least one $\sigma^E$ or $\sigma^E$-binding anti-sigma agent is encoded by a non-native form of SEQ ID NO:2 and SEQ ID NO:1, respectively, that reduces binding between the $\sigma^E$ and the anti-sigma agent, the non-native form of the $\sigma^E$ comprising at least one mutation selected from the group consisting of K38E, K38R, and M42A, the non-native form of the anti-sigma agent comprising at least one mutation selected from the group consisting of H6A, H31A, C35A, C35S, C38A, C38S, C38R and C187/189S, wherein the providing step comprises the step of introducing into SEQ ID NO:2 the at least one $\sigma^E$ mutation, thereby protecting the treated cells from damage in the presence of singlet oxygen, and
measuring protection of the treated cells from damage in the presence of singlet oxygen, wherein the protection is greater in the treated cells than in *Rhodobacter sphaeroides* cells in which binding between $\sigma^E$ and the anti-sigma agent is not reduced.

* * * * *

SEQUENCE LISTING

```
<160> NUMBER OF SEQ ID NOS: 9

<210> SEQ ID NO 1
<211> LENGTH: 213
<212> TYPE: PRT
<213> ORGANISM: Rhodobacter sphaeroides

<400> SEQUENCE: 1

Met Thr Ile Arg His His Val Ser Asp Ala Leu Leu Thr Ala Tyr Ala
1               5                   10                  15

Ala Gly Thr Leu Ser Glu Ala Phe Ser Leu Val Val Ala Thr His Leu
            20                  25                  30

Ser Leu Cys Asp Glu Cys Arg Ala Arg Ala Gly Ala Leu Asp Ala Val
        35                  40                  45

Gly Gly Ser Leu Met Glu Glu Thr Ala Pro Val Ala Leu Ser Glu Gly
    50                  55                  60

Ser Leu Ala Ser Val Met Ala Gln Leu Asp Arg Gln Ile Gln Arg Pro
65                  70                  75                  80

Ala Pro Ala Arg Arg Ala Asp Pro Arg Ala Pro Ala Pro Leu Ala Asp
                85                  90                  95

Tyr Val Gly Arg Arg Leu Glu Asp Val Arg Trp Arg Thr Leu Gly Gly
            100                 105                 110

Gly Val Arg Gln Ala Ile Leu Pro Thr Gly Gly Glu Ala Ile Ala Arg
        115                 120                 125

Leu Leu Trp Ile Pro Gly Gly Gln Ala Val Pro Asp His Gly His Arg
    130                 135                 140

Gly Leu Glu Leu Thr Leu Val Leu Gln Gly Ala Phe Arg Asp Glu Thr
145                 150                 155                 160

Asp Arg Phe Gly Ala Gly Asp Ile Glu Ile Ala Asp Gln Glu Leu Glu
                165                 170                 175

His Thr Pro Val Ala Glu Arg Gly Leu Asp Cys Ile Cys Leu Ala Ala
            180                 185                 190

Thr Asp Ala Pro Leu Arg Phe Asn Ser Phe Leu Pro Lys Leu Val Gln
        195                 200                 205

Pro Phe Phe Arg Ile
    210

<210> SEQ ID NO 2
<211> LENGTH: 181
```

```
<212> TYPE: PRT
<213> ORGANISM: Rhodobacter sphaeroides

<400> SEQUENCE: 2

Met Thr Asp Lys Ser Asp Arg Thr Asp Trp Val Ala Leu Met Arg Ala
1               5                   10                  15

Ile Arg Asp His Arg Asp Glu Ala Ala Phe Ala Glu Leu Phe Gln His
                20                  25                  30

Phe Ala Pro Lys Val Lys Gly Phe Leu Met Lys Ser Gly Ser Val Ala
            35                  40                  45

Ser Gln Ala Glu Glu Cys Ala Gln Asp Val Met Ala Thr Val Trp Gln
50                  55                  60

Lys Ala His Leu Phe Asp Pro Ser Arg Ala Ser Val Ala Thr Trp Ile
65                  70                  75                  80

Phe Thr Ile Ala Arg Asn Arg Arg Ile Asp Gly Leu Arg Lys Asp Arg
                85                  90                  95

Gln Pro Glu Pro Glu Asp Leu Phe Trp Gly Pro Asp Ser Glu Pro Asp
            100                 105                 110

Gln Ala Asp Val Tyr Glu Met Gln Gln Glu Asn Ala Arg Leu Gly Arg
        115                 120                 125

Ala Ile Ala Arg Leu Pro Glu Ala Gln Arg Ala Leu Ile Glu Arg Ala
    130                 135                 140

Phe Phe Gly Asp Leu Thr His Arg Glu Leu Ala Ala Glu Thr Gly Leu
145                 150                 155                 160

Pro Leu Gly Thr Ile Lys Ser Arg Ile Arg Leu Ala Leu Asp Arg Leu
                165                 170                 175

Arg Gln His Met Ser
            180

<210> SEQ ID NO 3
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 3
nrnvtsatcc rsvnndsbsb nbhnbsmgta                                      30

<210> SEQ ID NO 4
<211> LENGTH: 30
<212> TYPE: DNA
<213> ORGANISM: Artificial
<220> FEATURE:
<223> OTHER INFORMATION: Synthetic oligonucleotide
```

```
<220> FEATURE:
<221> NAME/KEY: misc_feature
<222> LOCATION: (7)..(24)
<223> OTHER INFORMATION: n is a, c, g, or t

<400> SEQUENCE: 4
tgatccnnnn nnnnnnnnnn nnnntagtga                                            30

<210> SEQ ID NO 5
<211> LENGTH: 29
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (6)..(23)
<223> OTHER INFORMATION: n is a, c, g, or t

<400> SEQUENCE: 5
gatccnnnnn nnnnnnnnnn nnntagtaa                                             29

<210> SEQ ID NO 6
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)..(24)
<223> OTHER INFORMATION: n is a, c, g, or t

<400> SEQUENCE: 6
tgatccnnnn nnnnnnnnnn nnnntatctg                                            30

<210> SEQ ID NO 7
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)..(24)
<223> OTHER INFORMATION: n is a, c, g, or t

<400> SEQUENCE: 7
tgatccnnnn nnnnnnnnnn nnnntaagaa                                            30

<210> SEQ ID NO 8
<211> LENGTH: 31
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (7)..(25)
<223> OTHER INFORMATION: n is a, c, g, or t

<400> SEQUENCE: 8
tcatccnnnn nnnnnnnnnn nnnnntagcc t                                          31

<210> SEQ ID NO 9
<211> LENGTH: 30
<212> TYPE: DNA
<213> ORGANISM: Artificial
<220> FEATURE:
<223> OTHER INFORMATION: Synthetic oligonucleotide
```

-continued

```
<220> FEATURE:
<221> NAME/KEY: misc_feature
<222> LOCATION: (7)..(24)
<223> OTHER INFORMATION: n is a, c, g, or t

<400> SEQUENCE: 9
tgatccnnnn nnnnnnnnnn nnnntaagag                                        30
```